United States Patent [19]
Jao et al.

[11] Patent Number: 5,690,211
[45] Date of Patent: Nov. 25, 1997

[54] CONTACT LENS CLEANER

[76] Inventors: Shu-Wen Jao, 2nd Fl., No. 16, Sec. 3, Tin-Jiou Rd.; Lee Wei, 5th Fl., No. 9, Alley 51, Lane 269, Sec. 3, Roosevelt Rd., both of Taipei City, Taiwan

[21] Appl. No.: 334,963

[22] Filed: Nov. 7, 1994

[51] Int. Cl.⁶ .................................................. B65D 3/04
[52] U.S. Cl. ........................ 206/5.1; 206/210; 134/901
[58] Field of Search .................... 206/5.1, 210; 422/113, 422/297, 300; 134/901

[56] References Cited

U.S. PATENT DOCUMENTS

| | | | |
|---|---|---|---|
| 4,750,610 | 6/1988 | Ryder | 206/5.1 |
| 4,889,693 | 12/1989 | Su et al. | 422/113 |
| 4,956,156 | 9/1990 | Kanner | 206/5.1 |
| 5,250,266 | 10/1993 | Kanner | 206/5.1 |
| 5,366,078 | 11/1994 | Braun | 134/901 |

*Primary Examiner*—David T. Fidei
*Attorney, Agent, or Firm*—Harrison & Egbert

[57] ABSTRACT

A new structure of contact lens cleaner provides a rotary structure which can be easily manufactured and assembled. It also provides a safe one-way air exhausting chamber which can prevent the cleaner from explosion and make it safe to the user, and it further provides a platinum reactor which is a structure easy to be set in the cleaner and easy for the user to mount or dismount it.

1 Claim, 6 Drawing Sheets

CONTACT LENS CLEANER

TECHNICAL FIELD

The present invention relates to devices for the cleaning of contact lenses. More particularly, the present invention relates to rotary-type contact lenses cleaning devices.

BACKGROUND OF THE INVENTION

In recent years, more and more people wear contact lenses. People think that wearing contact lenses makes them look more handsome or beautiful than wearing glasses. So in the future there will still be a great market for the products of contact lenses. However, now often consumers do not know how serious it is if a contact lens cleaner is not safe and sterile enough. People still use the conventional contact lens cleaners to clean their lenses.

A conventional lens cleaner does not exhaust completely the excessive oxygen out of the cleaner by means of isolating and dispensing the oxygen during the process of reaction, so the interior of the cleaner is easily contaminated. Then, even though it takes quite a long time to clean the lens, the cleaner still can not prevent itself from being contaminated by intruding materials after the reactor (platinum disc) and the cleaning solution (H2O2) are completely reacted in the cleaner (about 6 hrs). In other words, the assembly structure of the conventional lens cleaner is too complicated and is inefficient, and it is easy for contaminants to intrude into the conventional cleaner, so the consumer who wears a contact lens takes a risk of harming his own eyes. In view of this, the present invention is a lens cleaner which has a closed air chamber, a one-way exhaust vent, a rotary lens basket, and an easy mounting/dismounting reactor so that it is easy to produce the present lens cleaner which is safe to use and easy to mount and dismount for the consumer.

SUMMARY OF THE INVENTION

The contact lens, cleaner has a cover plate which can be set in a middle cover and between an upper rotary cover and the middle cover under the upper cover. A rotary gear box is disposed and secured between the middle cover and the cover plate. When the rotary cover is rotated to bring along a gear in it and the gear box will also be driven along so as to rotate a hanging basket under the middle cover. A vent is disposed in the upper portion of the middle cover. An independent air chamber is formed by five waits between the secured cover plate and the middle cover. An outward extending spout is disposed on the upper side wall of the air chamber.

A silicon rubber piece is disposed on the base plane of the middle cover, so the bottom surface of the air chamber is closed by the silicon rubber piece and the cleaner is isolated by it. A "U" shaped tongue is disposed on the silicon piece above the vent so that the excessive oxygen in the cleaner can be automatically exhausted out into the independent air chamber and will be exhausted by means of the outward extending spout.

Though the plastic reactor of the lens cleaner is shaped like a ring with a plurality of legs, it is the plastic reactor is received by a convex post in the lens cleaner. The reactor can easily match with the post and set in the cleaner. When the user wants to take the reactor out of the cleaner, he only has to press the reactor downwardly from its top and the reactor will be released from the convex past of the lens cleaner.

The first characteristic of the present invention is that it has an independent air chamber to prevent the exterior of the lens cleaner from being contaminated by outer impurities therefore.

The second characteristic is that it uses a silicon rubber piece to isolate an air chamber completely, and a tongue of the silicon rubber piece provides a one-way exhaust vent.

The third characteristic is that by means of a cover plate, a gear box is secured to the upper portion of the lens cleaner box and it only needs to add a gear to match with the upper rotary cover so as to amplify the rotation.

The fourth characteristic is that it makes the joining area between reactor and lens cleaner box as small as possible.

The last characteristic is that it provides an expanding space for the reactor so that the reactor can stretch its legs and depart from its position when it receives enough outer force.

The main object of the invention is to provide a sterile space in the lens cleaner so that it will not be contaminated by outer materials after the lens is cleaned by the reactor.

The other object of the invention is to provide the user with an easy way to remove the reactor without requiring the use of tools.

Still another object is to provide an inner cover plate to receive a gear box, and a gear and rotary cover to make this easily assembled structure have an effective operation for cleaning and promote the cleaning efficiency in the cleaning process.

DETAILED DESCRIPTION OF THE PREFERRED EMBODIMENTS

Figure 1:
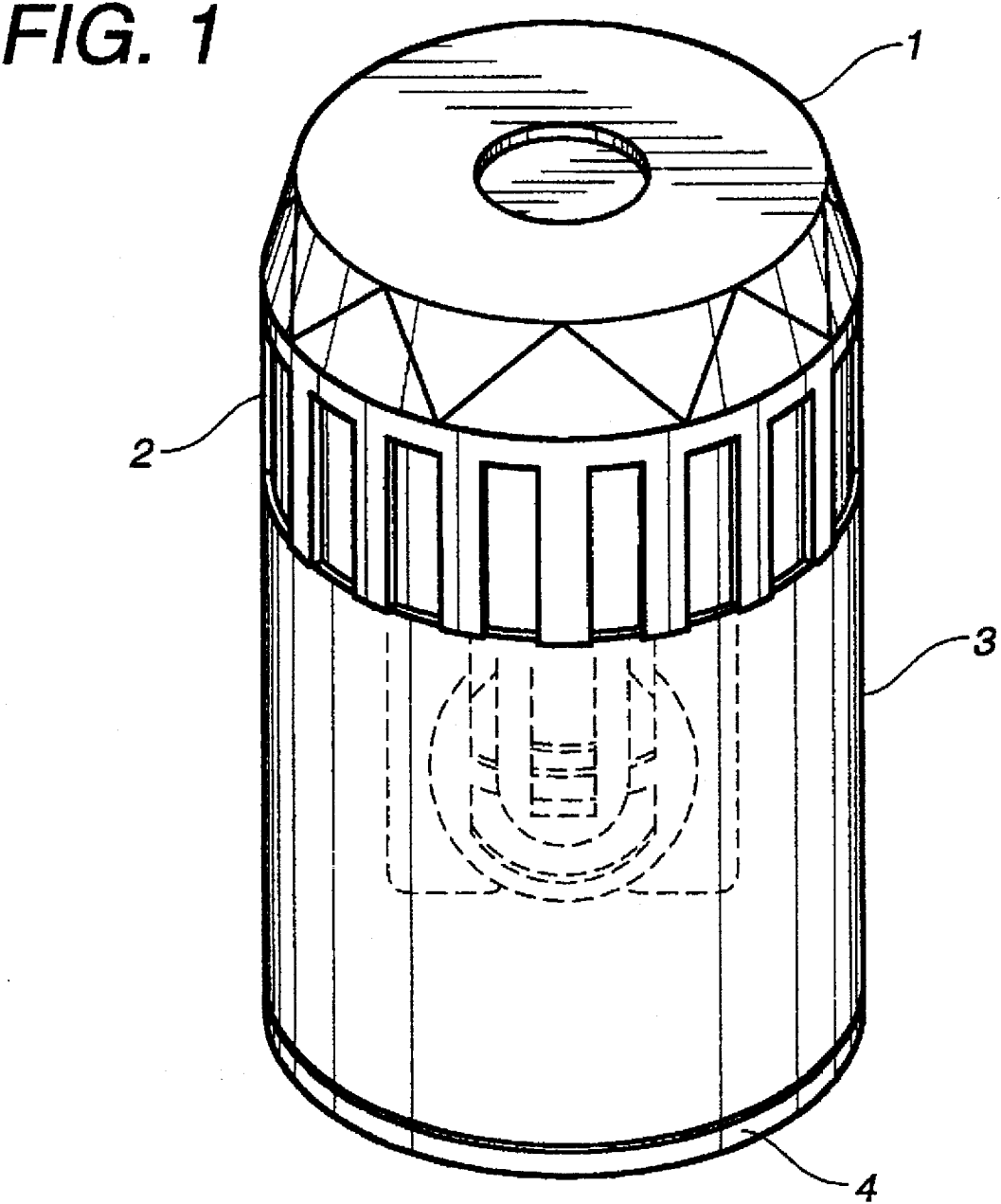
FIG. 1 is a view of the whole exterior body of an embodiment of the invention.
Figure 2:
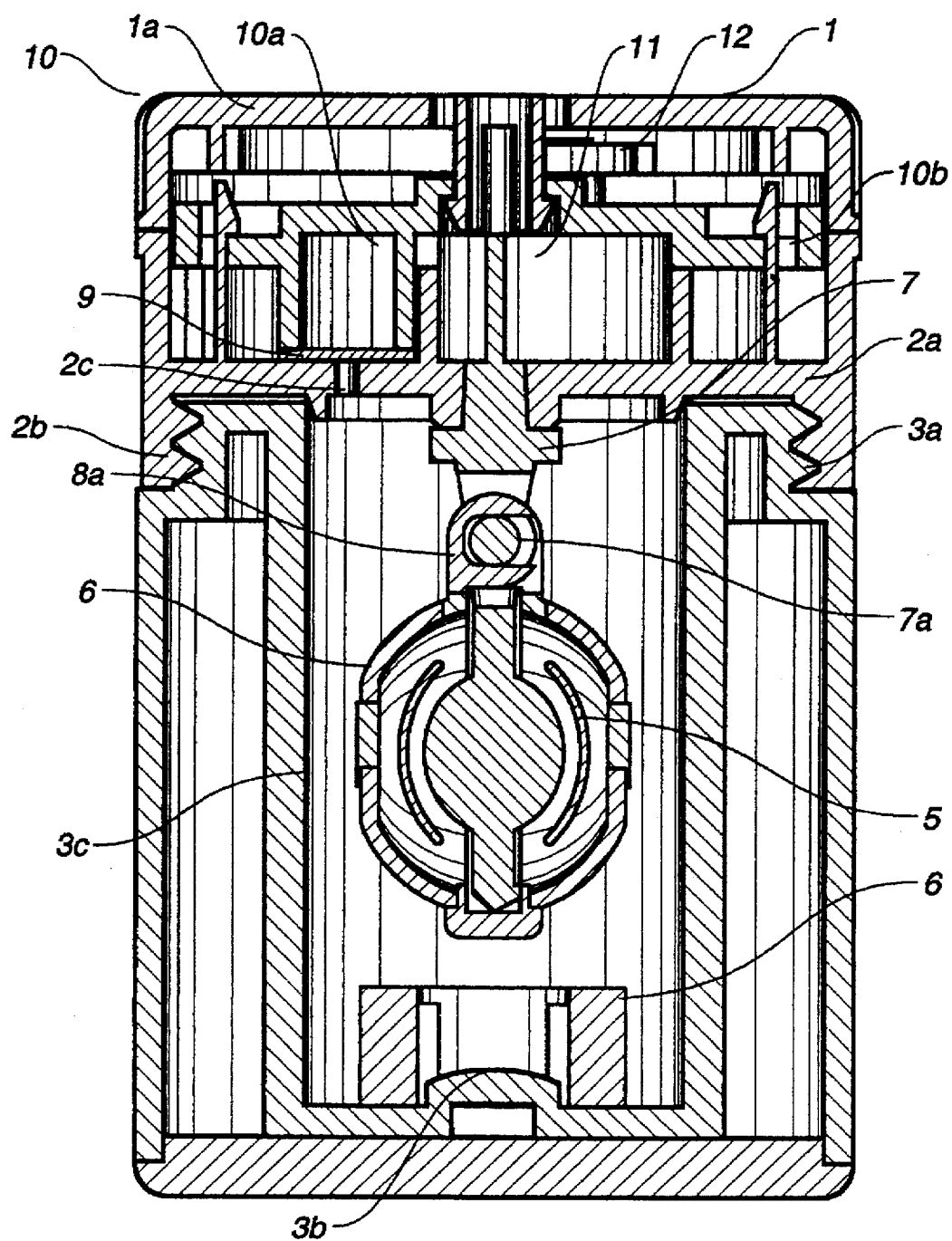
FIG. 2 is a sectional view of the embodiment of the invention.
Figure 3:
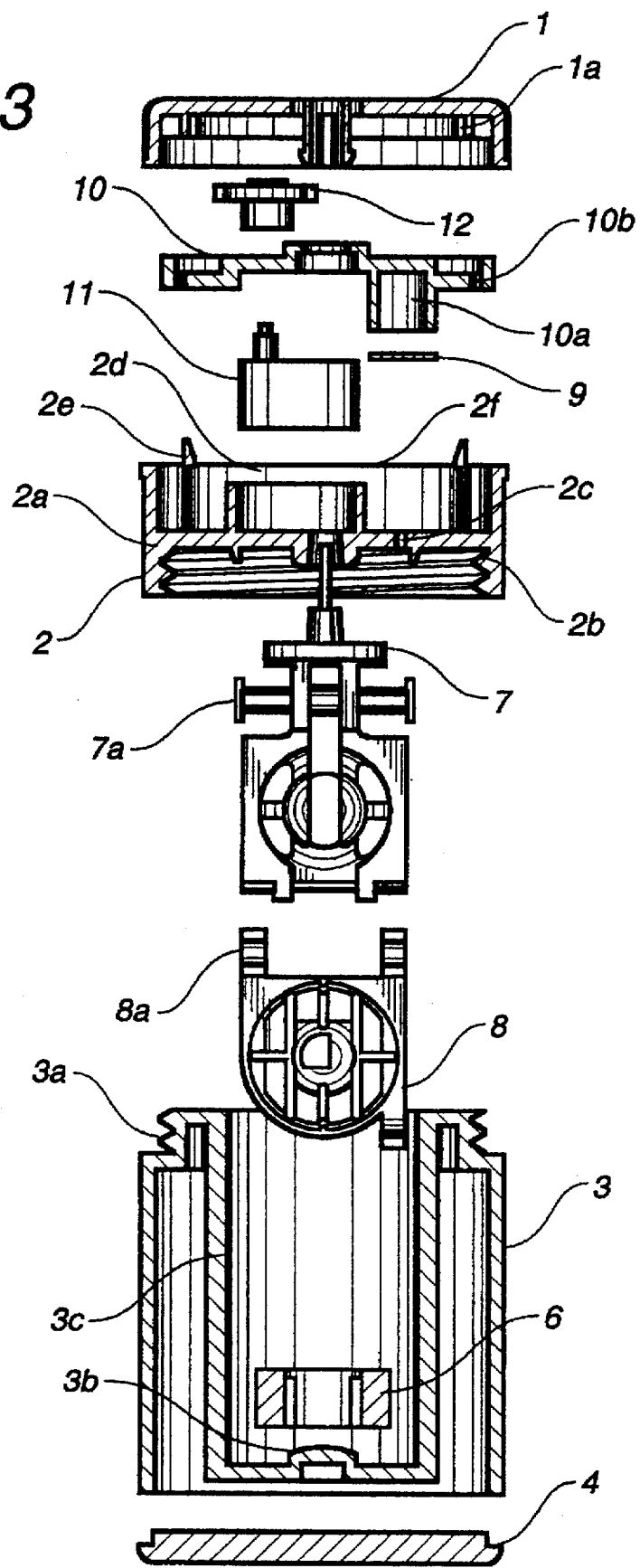
FIG. 3 is an exploded cross-sectional of the embodiment of the invention.

As shown in FIG 1, a view of the whole exterior body of an embodiment of the invention, the upper rotary cover 1 is a round shaped hollow housing made of plastic. The cover 1 has recessively corrugative decoration stripes on its outside so that it can be easily grasped and rotated by the user's fingers. Under the upper cover 1, there is disposed a middle cover 2 which is a plastic cylinder. A transverse plate 2a is disposed in the middle of the middle cover 2 to separate it into two parts (as shown in FIGS. 2 and 3) so that the inner and outer transmission structures of the cleaner can be isolated. Under the middle cover 2, there is disposed a transparent cylindrical water container 3. The container 3 has an inner container which is a cleaning area 3c with an opening on its top so that cleaning solutions can be put in. The container 3 has an opening at its bottom so that a side wall thread 3a can be disposed on the upper portion of the container 3. The bottom of the water container 3 is sealed by a bottom cover 4 which is shaped like a saucer.

FIG. 2 is a sectional view of the embodiment of the invention and FIG. 3 is a cross-sectional view of the whole body. There is disposed an inner thread 2b under the transverse panel 2a of the middle cover 2. The inner thread 2b can match with the thread 3a on the water container 3 so that they can be screwed together or unscrewed apart so that the user can easily put in or taken out the contact lens 5. Under the bottom of the cleaning area 3c in the water container 3, there is disposed a convex post 3b which can be fitted onto a ring-shaped reactor 6 having a plurality of legs. The reactor 6 is hollow and has an opening 6a at its side 6 so that it can keep its elasticity (now referring to FIGS. 6 and 7). The surface of the reactor is coated with platinum. When the cleaning solution (H2O2) is poured into the cleaning area 3c, the platinum will produce a lot of oxygen bubbles. The floating oxygen bubbles will clean and remove the foreign-substance on the contact lens 5. At the middle of the transverse panel 2a of the middle cover 2, there disposed a hole for a hanger 7 to insert in. Above the hanger 7, there is disposed a rotary shaft which can fit into the central hole of the transverse panel 2a. There is disposed a horizontal hanging shaft 7a under the rotary shaft. The hanging shaft 7a provides a pair of hanging baskets 8 with hanging opening, or closing. The hanger is made of plastics. It is shaped like a convex bowl with a vertical vent a joint shaft claw 8a is fitted to the hanging shaft 7a so that the lens 5 can be put between the hanger 7 and the hanging basket 8. When the lens is rotated, the oxygen bubbles will be mixed with the foreign substance on the contact lens so as to remove the foreign substance from the contact lens.

When the cleaning solution and the platinum coating on the reactor are reacted, oxygen bubbles will be produced in great quantities and are used to clean the contact lens 5. However, when they are reacting, neutralizing, and balancing each other, lots of oxygen bubbles continue to come out. In order to maintain the production of bubbles stably and prevent its inner air pressure from going up too high so as to explode, there is disposed a vent 2c on the transverse panel 2a of the middle cover. Around the outside of the vent, there is disposed a silicon rubber pad 9 on the vent 2c which has a tongue piece 9a shaped like a horseshoe. Actually the tongue piece 9a and the silicon rubber pad 9 belong to the same piece, but when the atmospheric pressure outside is equal to the inner air pressure in the cleaning room 3c of the water container 3, the tongue piece 9a will lie flat on the surface of the transverse panel 2a. When the air pressure in the cleaning area 3c is higher than outside air pressure, the tongue piece 9a will be blown open automatically. When these two pressures return to their balanced condition, the tongue piece 9a will return to its normal position.

Figure 4:
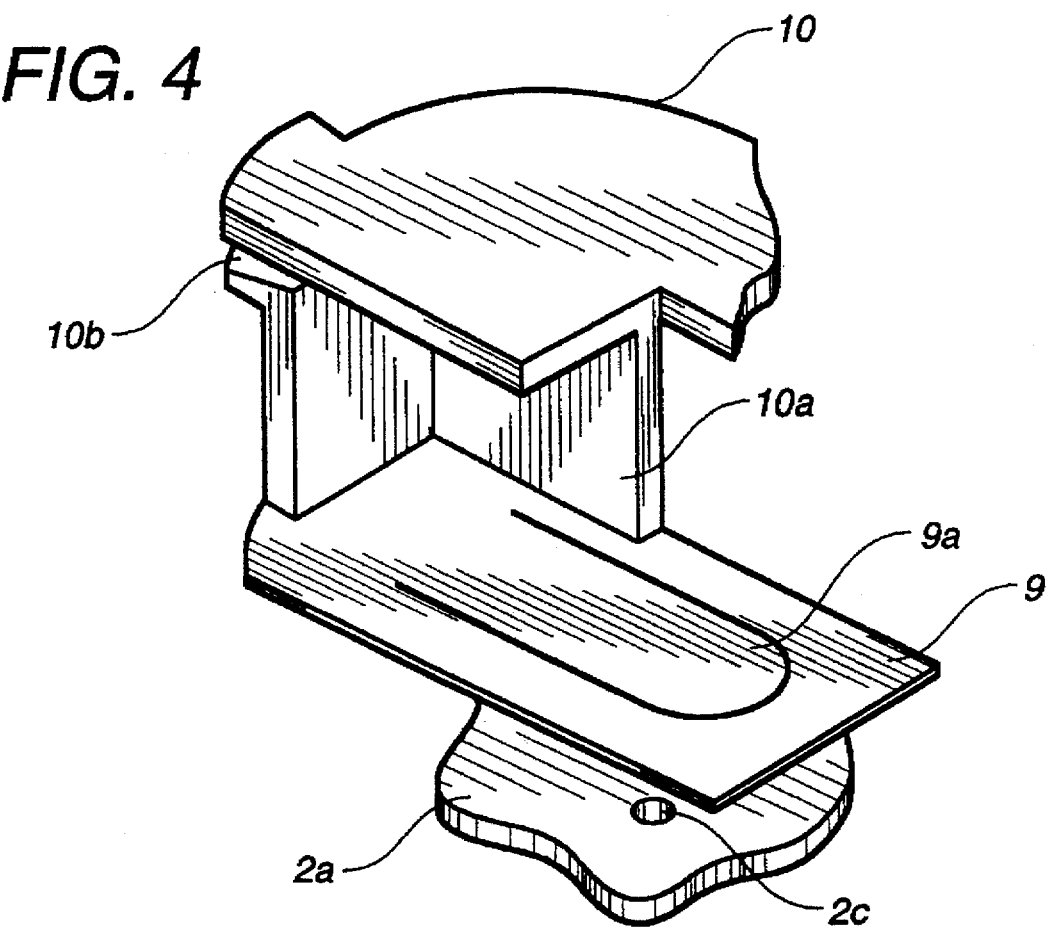
FIG 4 is a schematic pictorial view of an air chamber of the invention.
Figure 5:
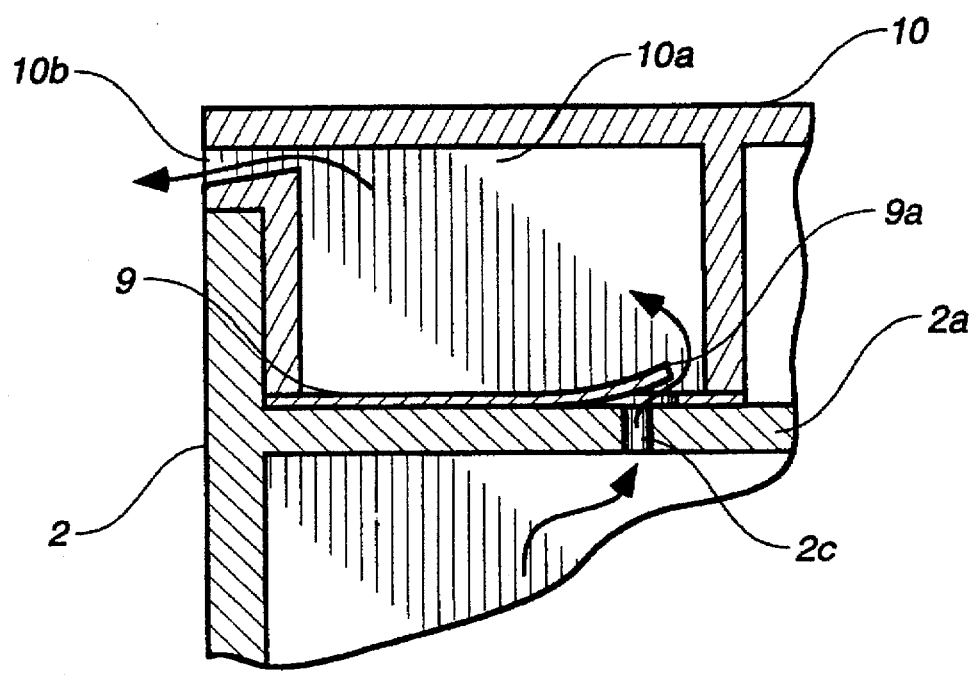
FIG. 5 is a schematic view of the exhaust air out of the air chamber.

Because the cleaning area 3c has no ability at all to protect itself from the intrusion of any bacteria after it finishes its sterilization, the area 3c can receive bacteria immediately, so the cleaning area 3c must be completely isolated from outside world. From this point of view, there is disposed an independent isolated air chamber 10, which is fixed under the cover plate 10 and above the middle cover 2. The cover plate 10 shaped like a soucer is made of plastics. Under the plate 10, there is formed a square air chamber 10a, which can press and attach on the silicon rubber pad 9 so as to close the air chamber 10a and to be independent and isolated from other transmission structures. In this way, the bubbles remaining in the air chamber 10a can be prevented from spreading into the other parts of the entire cleaner to result in a remaining pollution which may circulate back into the cleaning area 3c so as to result in secondary contamination. At the upper portion of the air chamber 10a, there is disposed an outward extending air spout 10b which extends to the upper flange of the middle cover 2. By means of the spout 10b, air in the air chamber 10a can be exhausted out of the cleaner. (as shown in FIGS. 4 and 5).

A rotary mechanism box 11 is fixed on the transverse panel 2a of the middle cover 2 so that the lens 5 can be washed clean by the bubbles and that the impurities on the lens 5 can be removed by the centrifugal force of the rotation. The rotary mechanism box 11 can be matched with the shaft on the top of a hanger 7 and thus can rotate the hanger 7. A recess 2d formed by surrounding walls is disposed on the transverse panel 2. The inner size of the recess 2d is sized for the rotary mechanism box 11 to set in. The rotary mechanism box 11 is covered and pressed by the bottom surface of the cover plate 10 and so the mechanism box is sealed by the cover plate 10. On two sides of the cover plate 10, there is disposed a pair of square holes 10b which can can receive a pair of hooks 2e on the transverse panel 2a of the middle cover 2 so as to connect the cover plate 10 and the middle cover 2.

There also is disposed a shaft hole on the cover plate 10 for a transmission gear 12 to penetrate. The transmission gear mates with an inner gear 1a in the upper rotary cover 1. Therefore, the rotary force of the upper rotary cover 1 can transmit its force to the rotary mechanism box 11 so as to rotate the hanger 7.

Figure 6:
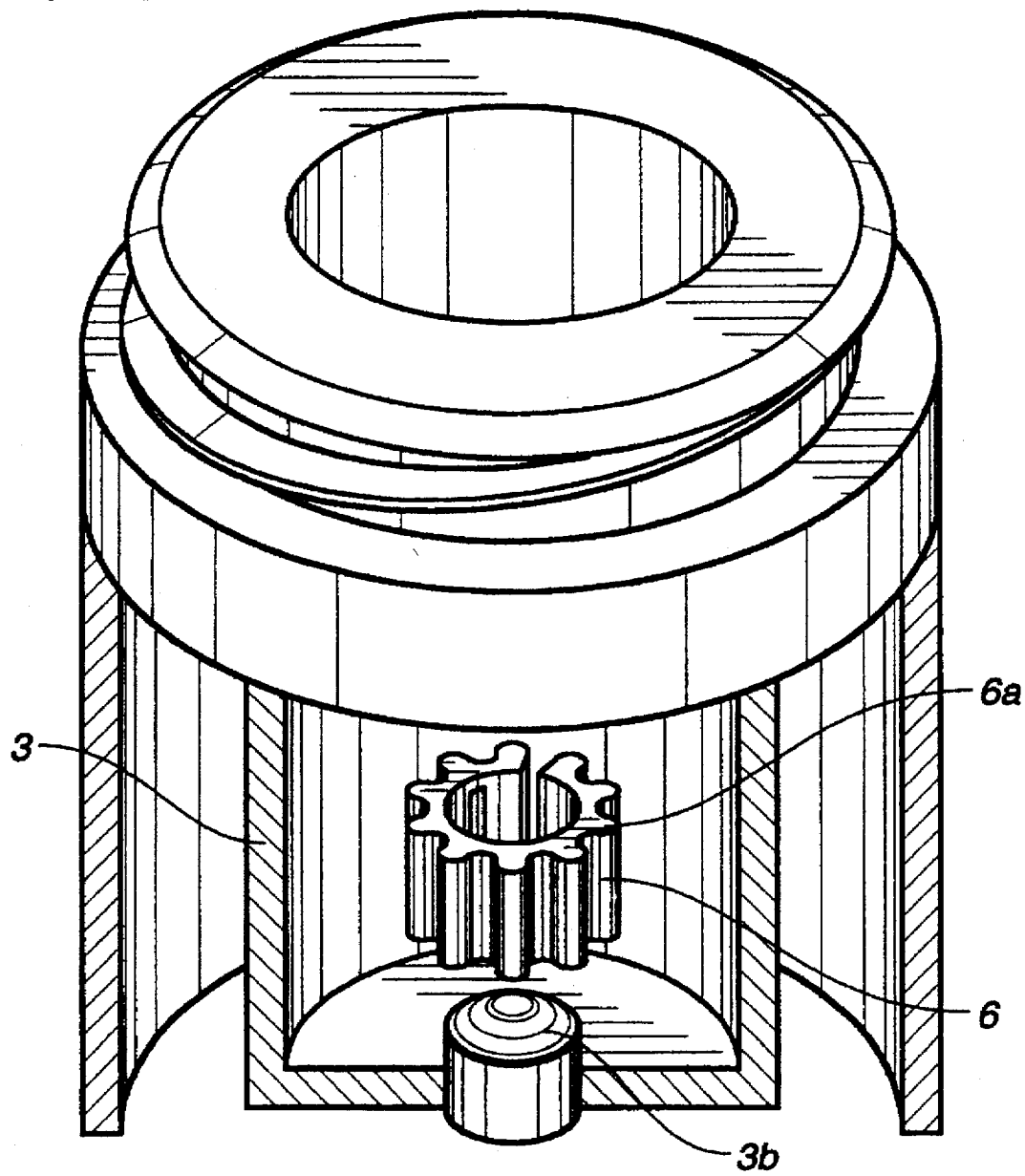
FIG. 6 is a view showing how the reactor is separated from the water container.
Figure 7:
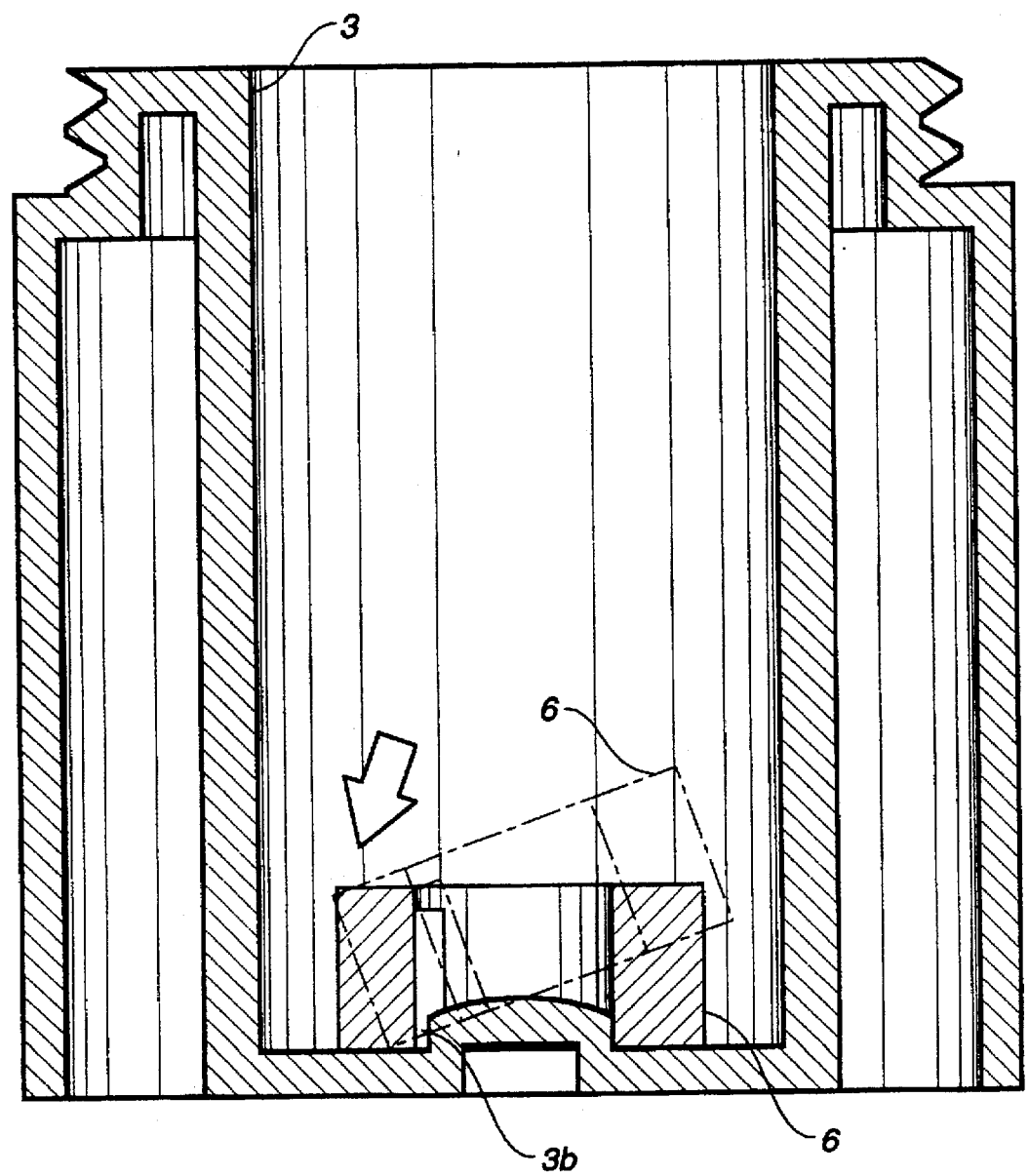
FIG. 7 is a sectional view of the assembly of the reactor and the water container.

As shown in FIG. 6, a view showing how the reactor is separated from the water container, and FIG. 7, a sectional view of the assembly of the reactor and the water container, there is disposed a cleaning container 3, which can receive the reactor at its bottom and can produce lots of cleaning bubbles to clean the lens in the hanging structure 7 in the container after the conventional cleaning solution is poured into it. The cleaning bubbles can pass through the aligned air exhausting holes on the lens hanging structure 7. At the bottom of the container, there is disposed a post with a convex upper surface so that the post 3b can be received in the recess of the inner wall surface of the cylindrical reactor. The height of the post 3b must be less than one-half the height of the reactor 6. The reactor 6, made of plastics, shaped like a ring, has a coating of platinum on its surface. The cylindrical reactor 6 has an indentation, and the inner diameter must be smaller than that of the post of the cleaning container 3 so that it can be easily taken out by pressing downwardly on the upper edge with fingers.

In conclusion, the structure of the present invention which provides a rotary mechanism, an independent air chamber, and a reactor which is easy to mount and dismount can really ensure the safety of the contact lens aster it is washed and cleaned in the lens cleaner. The present invention can do better sterilization, germ-killing, cleaning, and maintenance than the conventional lens cleaners. The rotary structure is easier and its reactor is more convenient to mount or dismount than the conventional one.

What is claimed is:

1. A contact lens cleaner comprising:

an upper rotary cover;

a middle cover;

an inner cover plate, said upper rotary cover covering said middle cover, said inner cover plate being disposed interior of said middle cover, said upper rotary cover and said middle cover and said inner cover plate defining a shell cover;

a gear linked to said upper rotary cover such that a rotation of said upper rotary cover rotates said gear;

a gear box disposed under said inner cover plate and coupled to said gear such that a rotation of said gear rotates said gear box, said inner cover plate having a recessed wall at a bottom of said inner cover plate, said recessed wall securing said gear box therein, said gear mating with an inner thread on an inner side of said upper rotary cover;

an air chamber formed by a transverse panel of said middle cover, said air chamber having an outward extending spout at one side, said transverse panel having two holes formed therein, one of said holes receiving a rotary shaft of said gear box, another of said holes begin an air-exhausting hole to said air chamber;

a cleaning container connected to said shell cover, said cleaning container receiving a lens-hanging structure therein, said lens-hanging structure connected to said gear box, said lens-hanging structure having air exhausting holes formed therein, said air exhausting holes of said lens-hanging structure having a flexible pad affixed thereover, said flexible pad for allowing air pressure above a desired level to pass therethrough, said cleaning container having a post with a convex upper surface at a bottom of said cleaning container;

a cylindrical plastic reactor having a platinum coating, said reactor having a recess therein, said recess receiving said post therein, said post having a height less than one-half a height of said reactor, said reactor being of a ring-shaped configuration, said reactor having an indentation with an inner diameter less than a diameter of said post, said pad being formed of a soft and elastic material, said pad having a tongue piece disposed over said air exhausting hole.

\* \* \* \* \*